(12) United States Patent
Carter et al.

(10) Patent No.: US 6,780,870 B2
(45) Date of Patent: Aug. 24, 2004

(54) PYRIMIDINE DERIVATIVES AS SELECTIVE INHIBITORS OF COX-2

(75) Inventors: Malcolm Clive Carter, London (GB); Alan Naylor, Stevenage (GB); Jeremy John Payne, Stevenage (GB); Neil Anthony Pegg, Sandy (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/182,788

(22) PCT Filed: Feb. 8, 2001

(86) PCT No.: PCT/GB01/00511

§ 371 (c)(1),
(2), (4) Date: Jul. 31, 2002

(87) PCT Pub. No.: WO01/58881

PCT Pub. Date: Aug. 16, 2001

(65) Prior Publication Data

US 2003/0109538 A1 Jun. 12, 2003

(30) Foreign Application Priority Data

Feb. 11, 2000 (GB) .............................. 0003224

(51) Int. Cl.$^7$ .................. C07D 239/42; C07D 401/12; A61K 31/505
(52) U.S. Cl. ................. 514/275; 544/330; 544/331; 544/332
(58) Field of Search ............... 544/330, 331, 544/332; 514/275

(56) References Cited

U.S. PATENT DOCUMENTS 6,020,343 A 2/2000 Belley et al. .............. 514/309

FOREIGN PATENT DOCUMENTS

| JP | 9241161 | 9/1997 |
|---|---|---|
| WO | WO 9607641 | 3/1996 |
| WO | WO 96 24585 | 8/1996 |
| WO | WO 96 41625 | 12/1996 |
| WO | WO 96 41645 | 12/1996 |
| WO | WO 98 03484 A | 1/1998 |
| WO | WO 98 16227 | 4/1998 |
| WO | WO 98 24782 A | 6/1998 |
| WO | WO 99 01439 | 1/1999 |
| WO | WO 01 38311 A2 | 5/2001 |
| WO | WO 01/38311 | 5/2001 |
| WO | WO 01/58881 | 8/2001 |

OTHER PUBLICATIONS

Simone, Oncology: Introduction, Cecil Textbook Of Medicine, 20th Edition, vol. 1, pp. 1004–1010, 1996.*
Layzer, Degenerative Diseases of the Nervous System, Cecil Textbook of Medicine, 20th Edition, vol. 2, pp. 2050–2057, 1996.*
Damasio, Alzheimer's Disease and Related Dementias, Cecil Textbook of Medicine, 20th Edition, vol. 2, pp. 1992–1996, 1996.*
Freston, PubMed Abstract (Am J Med 107(6A): 78S–88S; Discussion 89S), Dec. 1999.*
Naesdal et al., PubMed Abstract (Eur J Gastroenterol Hepatol, 13(12):1401–6), Dec. 2001.*
Douglas, Jr. Introduction to Viral Diseases, Cecil Textbook of Medicine, 20th Edition, vol. 2, pp. 1739–1747, 1996.*

* cited by examiner

*Primary Examiner*—Deepak Rao
(74) *Attorney, Agent, or Firm*—Lorie Ann Morgan

(57) ABSTRACT

The invention provides the compounds of formula (I)

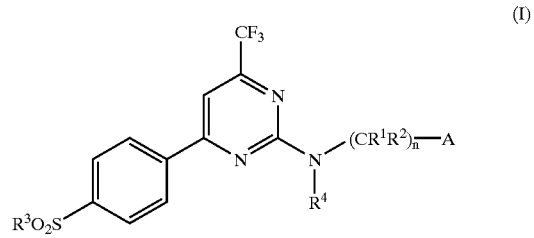

and pharmaceutically acceptable derivatives thereof, in which:

$R^1$ and $R^2$ are independently selected from H, or $C_{1-6}$alkyl;
$R^3$ is $C_{1-6}$alkyl or $NH_2$;
$R^4$ is H or $C_{1-6}$alkyl;
A is a 5- or 6-membered aryl, or a 5- or 6-membered aryl substituted by one or more $R^5$;
$R^5$ is halogen, $C_{1-6}$alkyl, $C_{1-6}$alkyl substituted by one ore more F, $C_{1-6}$alkoxy, $C_{1-6}$alkoxy substituted by one or more F, $SO_2NH_2$ or $SO_2C_{1-6}$alkyl; and
n is 1 to 4.

50 Claims, No Drawings

PYRIMIDINE DERIVATIVES AS SELECTIVE INHIBITORS OF COX-2

CROSS-REFERENCES TO RELATED APPLICATIONS

This application is a Rule 371 Application of PCT Application No. GB01/00511, filed Feb. 8, 2001, which claims priority to GB application Ser. No. 0003224.3, filed Feb. 11, 2000.

This invention relates to pyrimidine derivatives, to processes for their preparation, to pharmaceutical compositions containing them and to their use in medicine.

The enzyme cyclooxygenase (COX) has recently been discovered to exist in two isoforms, COX-1 and COX-2. COX-1 corresponds to the originally identified constitutive enzyme while COX-2 is rapidly and readily inducible by a number of agents including mitogens, endotoxin, hormones, cytokines and growth factors. Prostaglandins generated by the action of COX have both physiological and pathological roles. It is generally believed that COX-1 is largely responsible for the important physiological functions such as maintenance of gastrointestinal integrity and renal blood flow. In contrast the inducible form, COX-2, is believed to be largely responsible for the pathological effects of prostaglandins where rapid induction of the enzyme occurs in response to such agents as inflammatory agents, hormones, growth factors and cytokines. A selective inhibitor of COX-2 would therefore have anti-inflammatory, anti-pyretic and analgesic properties, without the potential side effects associated with inhibition of COX-1. We have now found a novel group of compounds which are both potent and selective inhibitors of COX-2.

DETAILED DESCRIPTION OF THE INVENTION

The invention thus provides the compounds of formula (I)

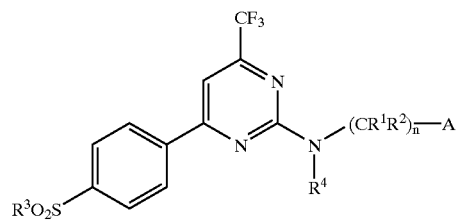

(I)

and pharmaceutically acceptable derivatives thereof, in which:

$R^1$ and $R^2$ are independently selected from H, or $C_{1-6}$alkyl;

$R^3$ is $C_{1-6}$alkyl or $NH_2$;

$R^4$ is H or $C_{1-6}$alkyl;

A is a 5- or 6-membered aryl, or a 5- or 6-membered aryl substituted by one or more $R^5$;

$R^5$ is halogen, $C_{1-6}$alkyl, $C_{1-6}$alkyl substituted by one or more F, $C_{1-6}$alkoxy, $C_{1-6}$alkoxy substitued by one or more F, $SO_2NH_2$ or $SO_2C_{1-6}$alkyl; and n is 1 to 4.

By pharmaceutically acceptable derivative is meant any pharmaceutically acceptable salt, solvate, ester or amide, or salt or solvate of such ester or amide, of the compounds of formula (I), or any other compound which upon administration to the recipient is capable of providing (directly or indirectly) a compound of formula (I) or an active metabolite or residue thereof.

It will be appreciated by those skilled in the art that the compounds of formula (I) may be modified to provide pharmaceutically acceptable derivatives thereof at any of the functional groups in the compounds. Of particular interest as such derivatives are compounds modified at the benzenesulphonamide function to provide metabolically labile benzenesulphonamides. Acylated benzenesulphonamide derivatives are of especial interest.

It will be appreciated by those skilled in the art that the pharmaceutically acceptable derivatives of the compounds of formula (I) may be derivatised at more than one position.

It will be further appreciated by those skilled in the art that benzenesulphonamide derivatives of formula (I) may be useful as intermediates in the preparation of compounds of formula (I), or as pharmaceutically acceptable derivatives of formula (I), or both.

It will be appreciated that, for pharmaceutical use, the salts referred to above will be the physiologically acceptable salts, but other salts may find use, for example in the preparation of compounds of formula (I) and the physiologically acceptable salts thereof.

Suitable pharmaceutically acceptable salts include: acid addition salts formed with inorganic or organic acids, preferably inorganic acids, e.g. hydrochlorides, hydrobromides and sulphates; and alkali metal salts, formed from addition of alkali metal bases, such as alkali metal hydroxides, e.g. sodium salts.

The term halogen is used to represent fluorine, chlorine, bromine or iodine.

The term 'alkyl' as a group or part of a group means a straight or branched chain alkyl group, for example a methyl, ethyl, n-propyl, i-propyl, n-butyl, s-butyl or t-butyl group.

The term 5-membered aryl means an aryl selected from the following:

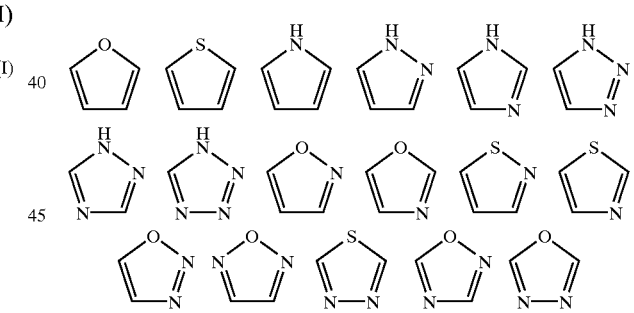

The term 6-membered aryl means aryl selected from:

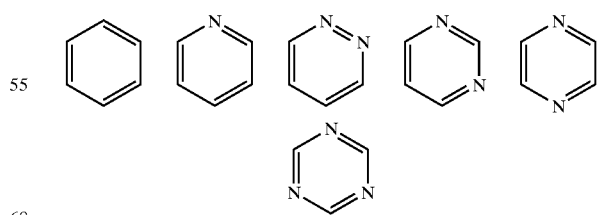

It will be appreciated by those skilled in the art that when $R^1$ and $R^2$ in formula (I) are different the corresponding compounds contain at least one chiral centre, by virtue of the asymmetric carbon atom defined thereby, and that such compounds exist in the form of a pair of optical isomers (i.e. enantiomers).

It is to be understood that the present invention encompasses all isomers of the compounds of formula (I) and their pharmaceutically acceptable derivatives, including all geometric, tautomeric and optical forms, and mixtures thereof (e.g. racemic mixtures).

In one aspect of the invention $R^1$ and $R^2$ are independently selected from H or methyl. In another aspect $R^1$ and $R^2$ are both H.

In another aspect of the invention $R^3$ is $C_{1-6}$alkyl, such as $C_{1-3}$alkyl (e.g. methyl).

In another aspect of the invention, $R^4$ is H or $C_{1-3}$alkyl, such as methyl.

In another aspect of the invention A is selected from

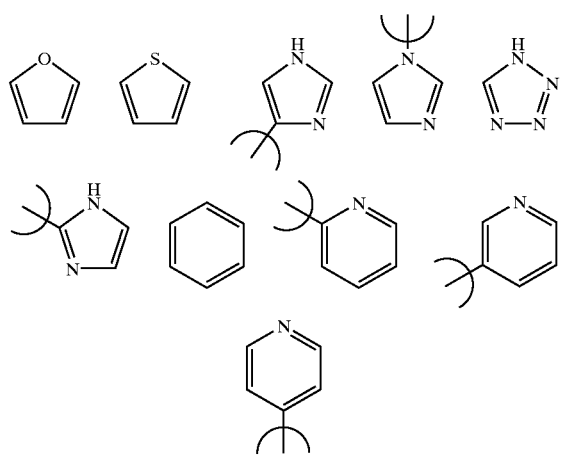

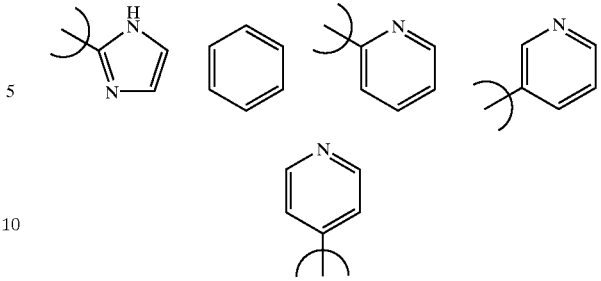

and A is unsubstituted or substituted by one or two $R^5$ (e.g. one $R^5$).

In another aspect of the invention A is selected from

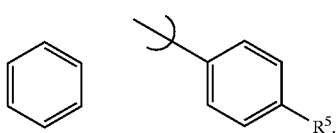

In another aspect of the invention $R^5$ is halogen (e.g. F), $C_{1-3}$alkyl (e.g. methyl), $C_{1-3}$alkyl substituted by one to three F (e.g. $CF_3$), $C_{1-3}$alkoxy (e.g. methoxy), $C_{1-3}$alkoxy substituted by one to three F (e.g. $OCHF_2$ or $OCF_3$), or $SONH_2$.

In another aspect of the invention $R^5$ is halogen (e.g. F) or $C_{1-6}$alkoxy, such as $C_{1-3}$alkoxy (e.g. methoxy).

In another aspect of the invention n is 1 to 3 (e.g. 1).

It is to be understood that the invention covers all combinations of particular aspects of the invention as described hereinabove.

Within the invention there is provided one group of compounds of formula (I) (group A) wherein: $R^1$ and $R^2$ are independently selected from H or methyl; $R^3$ is $C_{1-6}$alkyl, such as $C_{1-3}$alkyl (e.g. methyl); $R^4$ is H or $C_{1-3}$alkyl, such as methyl; A is selected from

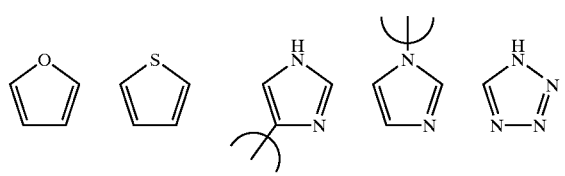

and is unsubstituted or substituted by one or two $R^5$ (e.g. one $R^5$); $R^5$ is halogen (e.g. F), $C_{1-3}$alkyl (e.g. methyl), $C_{1-3}$alkyl substituted by one to three F (e.g. $CF_3$), $C_{1-3}$alkoxy (e.g. methoxy), $C_{1-3}$alkoxy substituted by one to three F (e.g. $OCHF_2$ or $OCF_3$), or $SONH_2$; and n is 1 to 3 (e.g. 1).

Within the invention there is provided another group of compounds of formula (I) (group B) wherein: $R^1$ and $R^2$ are independently selected from H or methyl; $R^3$ is $C_{1-6}$alkyl, such as $C_{1-3}$alkyl (e.g. methyl); $R^4$ is H or $C_{1-3}$alkyl, such as methyl; A is selected from

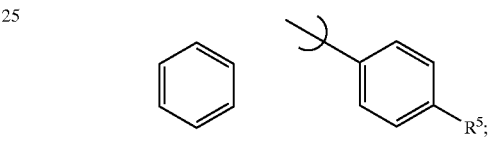

$R^5$ is halogen (e.g. F), $C_{1-3}$alkyl (e.g. methyl), $C_{1-3}$alkyl substituted by one to three F (e.g. $CF_3$), $C_{1-3}$alkoxy (e.g. methoxy), $C_{1-3}$alkoxy substituted by one to three F (e.g. $OCHF_2$ or $OCF_3$), or $SONH_2$; and n is 1 to 3 (e.g. 1).

Within the invention there is provided another group of compounds of formula (I) (group C) wherein: $R^1$ and $R^2$ are independently selected from H or methyl; $R^3$ is $C_{1-6}$alkyl, such as $C_{1-3}$alkyl (e.g. methyl); $R^4$ is H or $C_{1-3}$alkyl, such as methyl; A is selected from

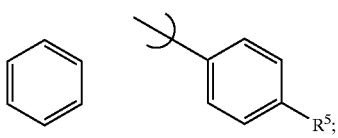

$R^5$ is halogen (e.g. F) or $C_{1-6}$alkoxy, such as $C_{1-3}$alkoxy (e.g. methoxy); and n is 1 to 3 (e.g. 1).

In another aspect of the invention, $R^1$ and $R^2$ in the compounds of groups A, B and C are both H.

In another aspect the invention provides the following compounds:

4-[4-(methylsulfonyl)phenyl]-N-(pyridin-4-ylmethyl)-6-(trifluoromethyl)pyrimidin-2-amine;
4-[4-(methylsulfonyl)phenyl]-N-(pyridin-3-ylmethyl)-6-(trifluoromethyl)pyrimidin-2-amine;
4-[4-(methylsulfonyl)phenyl]-N-(pyridin-2-ylmethyl)-6-(trifluoromethyl)pyrimidin-2-amine;
4-[4-(methylsulfonyl)phenyl]-N-(phenylmethyl)-6-(trifluoromethyl)-2-pyrimidinamine;
N-(4-methoxybenzyl)-4-[4-(methylsulfonyl)phenyl]-6-(trifluoromethyl)pyrimidin-2-amine;
N-(4-fluorobenzyl)-4-[4-(methylsulfonyl)phenyl]-6-(trifluoromethyl)pyrimidin-2-amine;

and pharmaceutically acceptable derivatives thereof.

Compounds of the invention are potent and selective inhibitors of COX-2. This activity is illustrated by their ability to selectively inhibit COX-2 over COX-1.

In view of their selective COX-2 inhibitory activity, the compounds of the present invention are of interest for use in human and veterinary medicine, particularly in the treatment of the pain (both chronic and acute), fever and inflammation of a variety of conditions and diseases mediated by COX-2. Such conditions and diseases are well known in the art and include rheumatic fever; symptoms associated with influenza or other viral infections, such as the common cold; lower back and neck pain; headache; toothache; sprains and strains; myositis; sympathetically maintained pain; synovitis; arthritis, including rheumatoid arthritis; degenerative joint diseases, including osteoarthritis; gout and ankylosing spondylitis; tendinitis; bursitis; skin related conditions, such as psoriasis, eczema, burns and dermatitis; injuries, such as sports injuries and those arising from surgical and dental procedures.

The compounds of the invention are also useful for the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; neuralgia, such as post-herpetic neuralgia and trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of the invention are also useful for the treatment of other conditions mediated by COX-2.

For example, the compounds of the invention inhibit cellular and neoplastic transformation and metastatic tumour growth and hence are useful in the treatment of certain cancerous diseases, such as colonic cancer and prostate cancer. The compounds of the invention are also useful in reducing the number of adenomatous colorectal polyps and thus reduce the risk of developing colon cancer. The compounds of the invention are also useful in the treatment of cancer associated with overexpression of HER-2/neu, in particular breast cancer.

Compounds of the invention also prevent neuronal injury by inhibiting the generation of neuronal free radicals (and hence oxidative stress) and therefore are of use in the treatment of stroke; epilepsy; and epileptic seizures (including grand mal, petit mal, myoclonic epilepsy and partial seizures).

Compounds of the invention also inhibit prostanoid-induced smooth muscle contraction and hence are of use in the treatment of dysmenorrhoea and premature labour.

Compounds of the invention are also useful in the treatment of liver disease, such as inflammatory liver disease, for example chronic viral hepatitis B, chronic viral hepatitis C, alcoholic liver injury, primary biliary cirrhosis, autoimmune hepatitis, nonalcoholic steatohepatitis and liver transplant rejection.

Compounds of the invention inhibit inflammatory processes and therefore are of use in the treatment of asthma, allergic rhinitis and respiratory distress syndrome; gastrointestinal conditions such as inflammatory bowel disease, Crohn's disease, gastritis, irritable bowel syndrome and ulcerative colitis; and the inflammation in such diseases as vascular disease, migraine, periarteritis nodosa, thyroiditis, aplastic anaemia, Hodgkin's disease, sclerodoma, type I diabetes, myasthenia gravis, multiple sclerosis, sorcoidosis, nephrotic syndrome, Bechet's syndrome, polymyositis, gingivitis, conjunctivitis and myocardial ischemia.

Compounds of the invention are also useful in the treatment of ophthalmic diseases such as retinitis, retinopathies, uveitis and of acute injury to the eye tissue.

Compounds of the invention are also useful for the treatment of cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Impairment.

According to a further aspect of the invention, we provide a compound of formula (I) or a pharmaceutically acceptable derivative thereof for use in human or veterinary medicine.

According to another aspect of the invention, we provide a compound of formula (I) or a pharmaceutically acceptable derivative thereof for use in the treatment of a condition which is mediated by COX-2.

According to a further aspect of the invention, we provide a method of treating a human or animal subject suffering from a condition which is mediated by COX-2 which comprises administering to said subject an effective amount of a compound of formula (I) or a pharmaceutically acceptable derivative.

According to a further aspect of the invention, we provide a method of treating a human or animal subject suffering from an inflammatory disorder, which method comprises administering to said subject an effective amount of a compound of formula (I) or a pharmaceutically acceptable derivative thereof.

According to another aspect of the invention, we provide the use of a compound of formula (I) or a pharmaceutically acceptable derivative thereof for the manufacture of a therapeutic agent for the treatment of a condition which is mediated by COX-2.

According to another aspect of the invention, we provide the use of a compound of formula (I) or a pharmaceutically acceptable derivative thereof for the manufacture of a therapeutic agent for the treatment of an inflammatory disorder.

It is to be understood that reference to treatment includes both treatment of established symptoms and prophylactic treatment, unless explicitly stated otherwise.

It will be appreciated that the compounds of the invention may advantageously be used in conjunction with one or more other therapeutic agents. Examples of suitable agents for adjunctive therapy include a $5HT_1$ agonist, such as a triptan (e.g. sumatriptan or naratriptan); an adenosine A1 agonist; an EP ligand (e.g. an EP4 antagonist); an NMDA modulator, such as a glycine antagonist; a sodium channel blocker (e.g. lamotrigine); a substance P antagonist (e.g. an $NK_1$ antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor α; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminium or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine. It is to be understood that the present invention covers the use of a compound of formula (I) or a pharmaceutically acceptable derivative thereof in combination with one or more other therapeutic agents.

The compounds of formula (I) and their pharmaceutically acceptable derivatives are conveniently administered in the form of pharmaceutical compositions. Thus, in another aspect of the invention, we provide a pharmaceutical composition comprising a compound of formula (I) or a pharmaceutically acceptable derivative thereof adapted for use in human or veterinary medicine. Such compositions may conveniently be presented for use in conventional manner in admixture with one or more physiologically acceptable carriers or excipients.

The compounds of formula (I) and their pharmaceutically acceptable derivatives may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable derivatives.

For oral administration, the pharmaceutical composition may take the form of, for example, tablets (including sublingual tablets), capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

As stated above, the compounds of the invention may also be used in combination with other therapeutic agents. The invention thus provides, in a further aspect, a combination comprising a compound of formula (I) or a pharmaceutically acceptable derivative thereof together with a further therapeutic agent.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A proposed daily dosage of a compound of formula (I) for the treatment of man is 0.01 mg/kg to 500 mg/kg, such as 0.05 mg/kg to 100 mg/kg, e.g. 0.1 mg/kg to 50 mg/kg, which may be conveniently administered in 1 to 4 doses. The precise dose employed will depend on the age and condition of the patient and on the route of administration. Thus, for example, a daily dose of 0.25 mg/kg to 10 mg/kg may be suitable for systemic administration.

Compounds of formula (I) and pharmaceutically acceptable derivatives thereof may be prepared by any method known in the art for the preparation of compounds of analogous structure.

Suitable methods for the preparation of compounds of formula (I) and pharmaceutically acceptable derivatives thereof follow. In Scheme 1 and its variations, $R^1$ to $R^4$, n and A are as defined in formula (I) above unless otherwise stated; Hal is a halogen, such as Cl or Br; MTBE is methyl t-butyl ether; and alkyl is a straight or branched chain alkyl group, for example a methyl, ethyl, n-propyl, i-propyl, n-butyl, s-butyl or t-butyl group.

Referring to Scheme 1, the treatment of compounds of formula (III) with an amine of formula (II) is conveniently carried out in a solvent, such as a nitrile (e.g. methylnitrile) and at elevated temperature (e.g. from about 50° C. to reflux). An excess of the amine may be used in place of the solvent.

Conveniently, the boronic acid coupling shown in Scheme 1 is carried out in a solvent, such as an ether (e.g. 1,2-dimethoxyethane); in the presence of a base, such as an inorganic base (e.g. sodium carbonate); and employing a palladium catalyst, such as tetrakis(triphenylphosphine)palladium(0).

Scheme 1
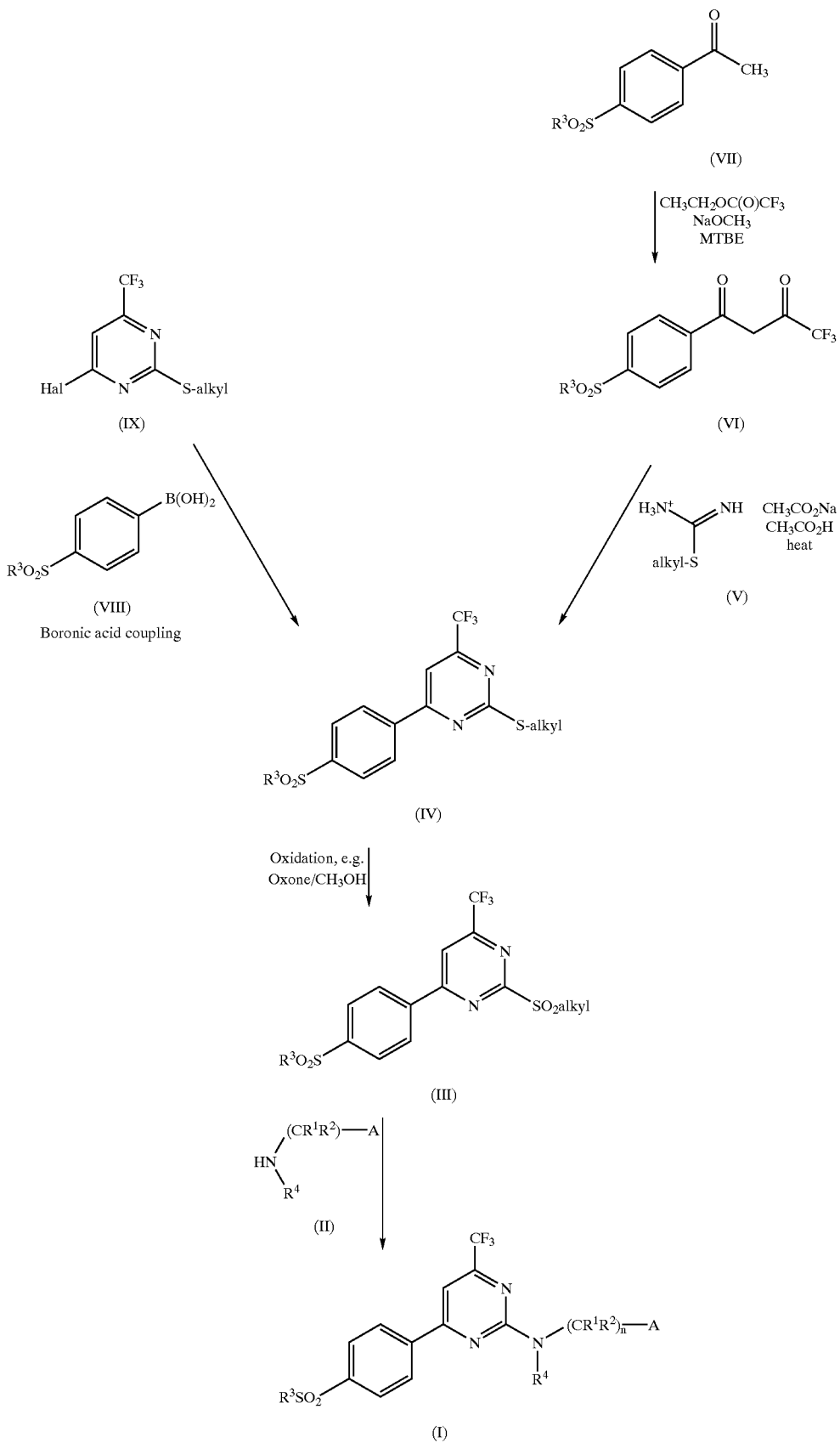

Conveniently the oxidation shown in Scheme 1 is effected using a monopersulfate compound, such as potassium peroxymonosulfate (known as Oxone™) and the reaction is carried out in a solvent, such as an aqueous alcohol, (e.g. aqueous methanol), and at between −78° C. and ambient temperature.

Referring to Scheme 1, the cyclisation of diones of formula (VI) to give the corresponding pyrimidines of formula (IV) is conveniently carried out employing a thioronium salt such as a 2-methyl-2-thiopseudourea sulfate and under reflux.

It will be appreciated by those skilled in the art that certain of the procedures described in Scheme 1 for the preparation of compounds of formula (I) or intermediates thereto may not be applicable to some of the possible substituents.

It will be further appreciated by those skilled in the art that it may be necessary or desirable to carry out the transformations described in Scheme 1 in a different order from that described, or to modify one or more of the transformations, to provide the desired compound of formula (I).

In one variation of Scheme 1 (scheme 1A), compounds of formula (III) wherein $R^3$ is $C_{1-6}$alkyl may be prepared by oxidising a disulphide of formula (IV)A:

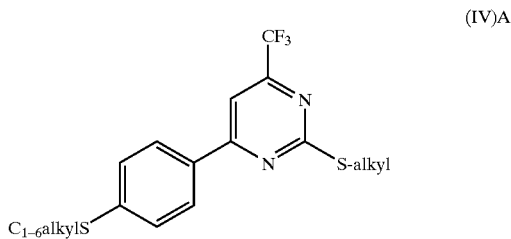

under oxidation conditions described hereinabove. Disulphides of formula (IV)A may be prepared according to the general procedures of Scheme 1 by employing sulphide derivatives in place of the corresponding alkylsulphonyl compounds of formulae (VII) and (VIII).

In another variation of scheme 1 (scheme 1B), compounds of formula (I) wherein $R^4$ is H may be prepared from the corresponding formamyl derivative, as illustrated below.

Scheme 1B

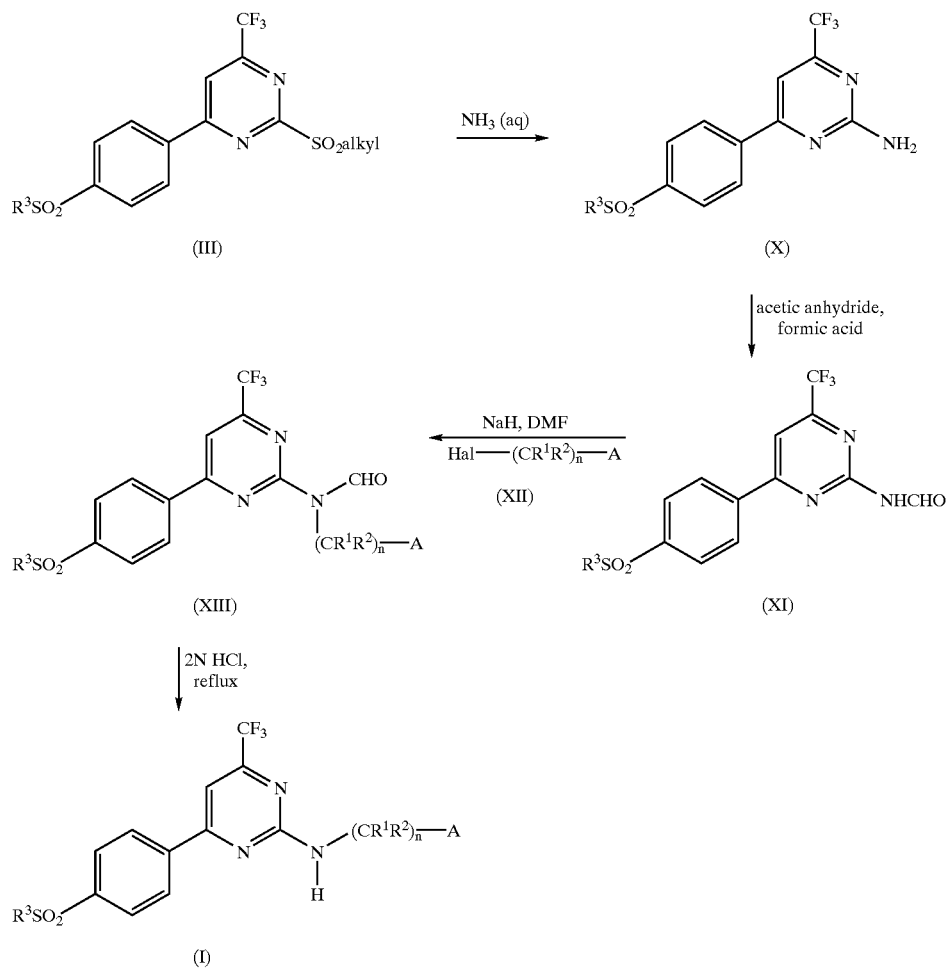

It will be appreciated by those skilled in the art that compounds of formula (I) may be prepared by interconversion, utilising other compounds of formula (I) as precursors. Suitable interconversions, such as alkylations, are well known to those skilled in the art and are described in many standard organic chemistry texts, such as 'Advanced Organic Chemistry' by Jerry March, fourth edition (Wiley, 1992), incorporated herein by reference. For example, compounds of formula (I) wherein $R^4$ is $C_{1-6}$alkyl may be prepared by alkylating the corresponding compound of formula (I) wherein $R^4$ is H.

Acylation of compounds of formula (I) wherein $R^3$ is $NH_2$ to provide corresponding acylated benzenesulphonamide derivatives may be carried out by conventional means, for example by employing conventional acylating agents such as those described in 'Advanced Organic Chemistry', pp 417–424.

As will be appreciated by those skilled in the art it may be necessary or desirable at any stage in the synthesis of compounds of formula (I) to protect one or more sensitive groups in the molecule so as to prevent undesirable side reactions. The protecting groups used in the preparation of compounds of formula (I) may be used in conventional manner. See, for example, those described in 'Protective Groups in Organic Synthesis' by Theodora W Green and Peter G M Wuts, second edition, (John Wiley and Sons, 1991), incorporated herein by reference, which also describes methods for the removal of such groups.

Amines of formula (II) are either known compounds or may be prepared by literature methods, such as those described in 'Comprehensive Organic Transformations: a guide to functional group preparations' by Richard Larock (VCH, 1989), incorporated herein by reference.

Thioronium salts of formula (V) are either known compounds or may be prepared by literature methods, such as those described in A H Owens et al, Eur J Med Chem, 1988, 23(3), 295–300, incorporated herein by reference Acetophenones of formula (VII) are either known compounds or may be prepared by conventional chemistry.

Boronic acids of formula (VIII) or derivatives thereof are either known compounds or may be prepared by literature methods, such as those described in EPA publication No. 533268; or R Miyaura et al, J Org Chem, 1995, 60, 7508–7510; each incorporated herein by reference.

4-Halo-6-trifluoromethylpyrimidines of formula (IX) are either known compounds or may be prepared by literature methods, such as those described in Japanese Patent no. 42014952 (Chem Abs ref CAN 68:105224), incorporated herein by reference.

Alkyl halides of formula (XII) are either known compounds or may be prepared by conventional chemistry.

Certain intermediates described above are novel compounds, and it is to be understood that all novel intermediates herein form further aspects of the present invention. Compounds of formulae (III), (IV) and (XIII) are key intermediates and represent a particular aspect of the present invention.

Conveniently, compounds of the invention are isolated following work-up in the form of the free base. Pharmaceutically acceptable acid addition salts of the compounds of the invention may be prepared using conventional means.

Solvates (e.g. hydrates) of a compound of the invention may be formed during the work-up procedure of one of the aforementioned process steps.

The Intermediates and Examples that follow illustrate the invention but do not limit the invention in any way. All temperatures are in ° C. Flash column chromatography was carried out using Merck 9385 silica. Solid Phase Extraction (SPE) chromatography was carried out using Varian Mega Bond Elut (Si) cartridges (Anachem) under 15 mmHg vacuum with stepped gradient elution. Thin layer chromatography (Tlc) was carried out on silica plates. In addition to those already defined, the following abbreviations are used: Me, methyl; Ac, acyl; DMSO, dimethylsulphoxide; TFA, trifluoroacetic acid; DME, dimethoxyethane; THF, tetrahydrofuran; DCM, dichloromethane; and MTBE, methyl t-butyl ether.

Intermediate 1

4,4,4-Trifluoro-1-[4-(methylthio)phenyl]butane-1,3-dione

To a solution of ethyl trifluoroacetate (7.95 ml, 1.1 eq) in MTBE (125 ml) was added dropwise 25% sodium methoxide in methanol (16 ml, 1.2 eq). 4-Methylthioacetophenone (Aldrich, 10 g, 0.06 mol) was added portionwise and the mixture stirred at ambient temperature overnight. 2N Hydrochloric acid (40 ml) was added cautiously and the organic phase separated, washed with brine and dried ($Na_2SO_4$) to give an orange solid. The orange solid was recrystallised from hot isopropanol to give the title compound as a yellow crystalline solid (11.25 g, 71%).

MH−261

Intermediate 2

2-(Methylthio)-4-[4-(methylthio)phenyl]-6-(trifluoromethyl) pyrimidine

To a mixture of 4,4,4-trifluoro-1-[4-(methylthio)phenyl] butane-1,3-dione (5 g) and 2-methyl-2-thiopseudourea sulfate (5.1 g, 0.98 eq) in acetic acid (100 ml) was added sodium acetate (3 g, 2 eq) and heated under reflux for 8 h. The mixture was concentrated in vacuo and water (100 ml) added to give a solid, which was isolated by filtration to give the title compound as a yellow solid (5.8 g, quantitative).

MH+317

Intermediate 3

2-(Methylthio)-4-[4-(methylthio)phenyl]-6-(trifluoromethyl) pyrimidine

A mixture of 4-chloro-2-methylthio-6-(trifluoromethyl) pyrimidine (ButtPark Ltd, 2.86 g, 14.55 mmol), 4-(methylthio)phenylboronic acid (Aldrich, 2.83 g, 1.1 eq), tetrakistriphenylphosphine palladium (0) (0.2 g) and sodium carbonate (4.04 g, 2.6 eq) in DME (200 ml) and water (100 ml) was heated under reflux with stirring under $N_2$ for 24 h. The reaction mixture was concentrated in vacuo and the resultant mixture partitioned between ethyl acetate and water. The organic phase was separated, washed with water, dried ($Na_2SO_4$) and concentrated in vacuo to a purple solid. Purification by flash column chromatography with cyclohexane:ethyl acetate as (6:1) as eluant gave the title compound as a yellow crystalline solid (3.86 g, 84%).

MH+317

Tlc $SiO_2$ cyclohexane:ethyl acetate (3:1) Rf 0.75 $uv_{254}$

Intermediate 4

2-(Methylsulfonyl)-4-[4-(methylsulfonyl)phenyl]-6-(trifluoromethyl)pyrimidine

To a solution of 2-(methylthio)-4-[4-(methylthio)phenyl]-6-(trifluoromethyl) pyrimidine (5.78 g) in MeOH (500 ml) was added a solution of OXONE™ (Aldrich, 56.23 g, 5 eq) in water (200 ml). The mixture was stirred at ambient temperature overnight, concentrated in vacuo and the residue partitioned between water and ethyl acetate (2×100 ml). The combined organic phases were dried and concentrated in vacuo to an off-white solid which was triturated with hot isopropanol to give the title compound as a white solid (5.6 g, 80%).

MH+381

Tlc $SiO_2$ Ethyl acetate:cyclohexane (1:1) Rf 0.45

Intermediate 5

4-[4-(methylsulfonyl)phenyl]-6-(trifluoromethyl)pyrimidin-2-amine

A solution of 2-(methylsulfonyl)-4-[4-(methylsulfonyl) phenyl]-6-(trifluoromethyl)pyrimidine (2 g, 5.258 mmol) in acetonitrile (30 ml) was treated with 0.880 ammonia (6 ml) dropwise. The resulting mixture was then stirred at 20 C. for 18 h. This gave the title compound as a colourless precipitate which was collected by filtration and dried (1.53 g)
MH−=316

Intermediate 6
4-[4-(methylsulfonyl)phenyl]-6-(trifluoromethyl)pyrimidin-2-ylformamide A mixture of formic acid (7 ml) and acetic anhydride (2 ml) was stirred at 20 C for 1 h. 4-[4-(Methylsulfonyl)phenyl]-6-(trifluoromethyl)pyrimidin-2-amine (0.5 g, 1.576 mmol) was then added and stirring was continued at ambient temperature for 18 h. This gave the title compound as a colourless precipitate which was collected by filtration and dried (0.32 g).
MH+=346

Intermediate 7
(5-methyl-1H-imidazol-4-yl)methyl[4-[4-(methylsulfonyl)phenyl]-6-(trifluoromethyl)pyrimidin-2yl]formamide To a stirred solution of 4-[4-(methylsulfonyl)phenyl]-6-(trifluoromethyl)pyrimidin-2-ylformamide (0.5 g, 1.54 mmol) in dry dimethylformamide (10 ml) under $N_2$ was added sodium hydride (60% dispersion in oil, 0.16 g). The mixture was stirred for 30 mins, 4-(chloromethyl)-5-methyl-1H-imidazole, hydrochloride (0.283 g) was added and stirring was then continued at room temp for 18 h. The mixture was then partitioned between water and ethyl acetate. The extracts were dried ($Na_2SO_4$) and evaporated. The residue was then triturated with diethyl ether giving the crude title compound as a pale yellow solid (0.27 g).
MH+=440

EXAMPLE 1
4-[4-(Methylsulfonyl)phenyl]-N-(pyridin-4-ylmethyl)-6-(trifluoromethyl)pyrimidin-2-amine To a stirred solution of 2-(methylsulfonyl)-4-[4-(methylsulfonyl)phenyl]-6-(trifluoromethyl)-pyrimidine (0.10 g, 0.26 mmol) in MeCN (4 ml) was added 4-(aminomethyl)-pyridine (0.14 ml, 5 eq) and the resultant solution heated under reflux for 18 h. The cooled reaction mixture was concentrated in vacuo and purified by SPE chromatography using chloroform, diethyl ether, ethyl acetate, acetone and methanol as the eluotropic series of solvents. Concentration in vacuo of the combined fractions containing pure product gave the title compound as a colourless solid (0.061 g, 57%).
MH+409.

EXAMPLE 2
4-[4-(Methylsulfonyl)phenyl]-N-(pyridin-3-ylmethyl)-6-(trifluoromethyl)pyrimidin-2-amine To a stirred solution of 2-(methylsulfonyl)-4-[4-(methylsulfonyl)phenyl]-6-(trifluoromethyl)pyrimidine (0.10 g, 0.26 mmol) in MeCN (3 ml) was added 3-(aminomethyl)-pyridine (169 mg, 6 eq) and the resultant solution heated under reflux for 3 h. The cooled reaction mixture was concentrated in vacuo and the resulting oil purified by SPE chromatography with chloroform then chloroform:methanol (50:1) as eluant. This gave the title compound as a yellow solid (100 mg, 93%).
MH+409.

EXAMPLE 3
4-[4-(Methylsulfonyl)phenyl]-N-(pyridin-2-ylmethyl)-6-(trifluoromethyl)pyrimidin-2-amine To a stirred solution of 2-(methylsulfonyl)-4-[4-(methylsulfonyl)phenyl]-6-(trifluoromethyl)pyrimidine (0.10 g, 0.26 mmol) in MeCN (4 ml) was added 2-(aminomethyl)-pyridine (0.14, 5 eq) and the resultant solution heated under reflux for 3 h. The cooled reaction mixture was concentrated in vacuo and purified by SPE chromatography using chloroform, diethyl ether, ethyl acetate, acetone and methanol as the eluotropic series of solvents. Concentration in vacuo of the combined fractions containing pure product gave the title compound as a colourless solid (0.086 g, 80%).
MH+409.

EXAMPLE 4
4-[4-(Methylsulfonyl)phenyl]-N-(phenylmethyl)-6-(trifluoromethyl)-2-pyrimidinamine To a stirred solution of 2-(Methylsulfonyl)-4-[4-(methylsulfonyl)phenyl]-6-(trifluoromethyl)pyrimidine (0.10 g, 0.26 mmol) in MeCN (4 ml) was added benzylamine (5 eq) and the resultant solution heated under reflux for 24 h. The cooled reaction mixture was concentrated in vacuo and purified by SPE chromatography with cyclohexane:ethyl acetate (3:1). Concentration in vacuo of the combined fractions containing pure product gave the title compound as a white solid (0.090 g, 80%).
MH+407.

The Examples of Table 1 were prepared in the manner described for Examples 1 to 4.

TABLE 1

(I)

| Ex | n | $R^1$ | $R^2$ | $R^3$ | $R^4$ | A | MS |
|----|---|-------|-------|-------|-------|---|-----|
| 5  | 1 | (1R)—$CH_3$ | H | $CH_3$ | H | phenyl | MH + 422 |
| 6  | 1 | (1S)—$CH_3$ | H | $CH_3$ | H | phenyl | MH + 422 |
| 7  | 1 | $CH_3$ | $CH_3$ | $CH_3$ | H | phenyl | MH + 436 |
| 8  | 1 | H | H | $CH_3$ | H | 3-methoxyphenyl | no ion |
| 9  | 1 | H | H | $CH_3$ | H | 4-methoxyphenyl | MH + 438 |
| 10 | 1 | H | H | $CH_3$ | H | 4-trifluoromethoxyphenyl | MH + 492 |
| 11 | 1 | H | H | $CH_3$ | H | 3,4-difluorophenyl | MH + 444 |
| 12 | 1 | H | H | $CH_3$ | H | 4-trifluoromethylphenyl | MH + 476 |
| 13 | 1 | H | H | $CH_3$ | H | 4-methylphenyl | MH + 422 |
| 14 | 1 | H | H | $CH_3$ | H | 3-fluorophenyl | MH + 426 |
| 15 | 1 | H | H | $CH_3$ | H | 4-fluorophenyl | MH + 426 |
| 16 | 1 | H | H | $CH_3$ | H | 3,5-difluorophenyl | MH + 444 |
| 17 | 1 | H | H | $CH_3$ | H | 2,5-difluorophenyl | MH + 444 |
| 18 | 1 | H | H | $CH_3$ | H | 2,6-difluorophenyl | MH + 444 |
| 19 | 1 | H | H | $CH_3$ | H | 2,4-difluorophenyl | MH+ 444 |
| 20 | 1 | H | H | $CH_3$ | H | 4-difluoromethoxyphenyl | MH + 474 |
| 21 | 1 | H | H | $CH_3$ | H | 3-methylphenyl | MH + 422 |

TABLE 1

(I)

[Structure: 4-(trifluoromethyl)-6-[4-(R³O₂S)phenyl]-N-R⁴-N-[(CR¹R²)ₙ-A]pyrimidin-2-amine]

| Ex | n | R¹ | R² | R³ | R⁴ | A¹ | MS |
|----|---|----|----|----|----|----|-----|
| 22 | 1 | H | H | CH₃ | H | 2-fluorophenyl | MH + 426 |
| 23 | 1 | H | H | CH₃ | H | 3-chlorophenyl | MH + 442 |
| 24 | 2 | H | H | CH₃ | H | 2-pyridyl | MH + 423 |
| 25 | 1 | H | H | CH₃ | H | 2-furyl | MH + 398 |
| 26 | 1 | H | H | CH₃ | CH₃ | phenyl | MH + 422 |
| 27 | 3 | H | H | CH₃ | H | phenyl | MH + 426 |
| 28 | 1 | H | H | CH₃ | H | 5-methyl-2-thienyl | MH + 428 |
| 29 | 1 | H | H | CH₃ | H | 4-methyl-2-thiazolyl | MH + 429 |

EXAMPLE 30

N-(4-methoxybenzyl)-4-[4-(methylsulfonyl)phenyl]-6-(trifluoromethyl)pyrimidin-2-amine A stirred solution of 2-(methylsulfonyl)-4-[4-(methylsulfonyl)phenyl]-6-(trifluoromethyl)pyrimidine (1 g, 2.629 mmol) in N-methylpyrrolidone (10 ml) was treated with 4-methoxybenzylamine (0.69 ml). The mixture was stirred at room temperature for 18 h and was then diluted with water (50 ml). This gave a cream solid, which was triturated with diethyl ether giving the title compound as a colourless solid (0.98 g).

MH+=438

EXAMPLE 31

N-(4-fluorobenzyl)-4-[4-(methylsulfonyl)phenyl]-6-(trifluoromethyl)pyrimidin-2-amine A stirred solution of 2-(methylsulfonyl)-4-[4-(methylsulfonyl)phenyl]-6-(trifluoromethyl)pyrimidine (1 g, 2.629 mmol) in N-methylpyrrolidone (10 ml) was treated with 4-fluorobenzylamine (0.60 ml). The mixture was stirred at room temp for 18 h and was then diluted with water (50 ml). This gave the title compound as a colourless solid which was collected by filtration and dried (0.72 g).

MH+=426.

The Examples of Table 2 were prepared in the manner described for Examples 30 and 31.

TABLE 2

(I)

| Ex | n | R¹ | R² | R³ | R⁴ | A | MS |
|----|---|----|----|----|----|----|-----|
| 32 | 1 | H | H | CH₃ | H | 1,5-dimethyl-2-pyrrolyl | MH + 425 |
| 33 | 1 | H | H | CH₃ | H | 3-methyl-2-thienyl | MH + 428 |
| 34 | 1 | H | H | CH₃ | H | 3-thienyl | MH + 414 |

TABLE 2-continued (I)

| Ex | n | R¹ | R² | R³ | R⁴ | A | MS |
|----|---|----|----|----|----|----|-----|
| 35 | 1 | H | H | CH₃ | H | 5-methyl-2-furanyl | MH + 412 |
| 36 | 1 | H | H | CH₃ | H | 6-methyl-2-pyridyl | MH + 423 |

EXAMPLE 37

N-[(5-methyl-1H-imidazol-4-yl)methyl]-4-[4-(methylsulfonyl)phenyl]-6-(trifluoromethyl)pyrimidine-2-amine A solution of crude (5-methyl-1H-imidazol-4-yl)methyl [4-[4-(methylsulfonyl)phenyl]-6-(trifluoromethyl)pyrimidin-2yl]formamide (0.27 g, 0.615 mmol) in ethanol (10 ml) and 2N hydrochloric acid (10 ml) was heated under reflux for 2 h. The solvents were then evaporated and the residue basified with 0.880 ammonia and extracted with DCM. The dried organic phase was evaporated onto silica gel and this mixture was purified on a silica gel SPE cartridge. Elution with DCM:ethanol:0.880 ammonia, 91:8:1, gave the title compound as a colourless crystalline solid (0.14 g).

MH+=412.

The Examples of Table 3 were prepared in the manner described for Example 37.

TABLE 3

(I)

| Ex | n | R¹ | R² | R³ | R⁴ | A | MS |
|----|---|----|----|----|----|----|-----|
| 38 | 1 | H | H | CH₃ | H | 5-methyl-4-(1H)imidazolyl | MH + 412 |
| 39 | 1 | H | H | CH₃ | H | 5-methyl-3-isoxazolyl | MH + 413 |
| 40 | 1 | H | H | CH₃ | H | 2-fluoro-4-pyridyl | MH + 455 |

| Example 41 - Tablets | | |
|---|---|---|
| a) | Compound of the invention | 5.0 mg |
| | Lactose | 95.0 mg |
| | Microcrystalline Cellulose | 90.0 mg |
| | Cross-linked polyvinylpyrrolidone | 8.0 mg |
| | Magnesium Stearate | 2.0 mg |
| | Compression weight | 200.0 mg |

The compound of the invention, microcrystalline cellulose, lactose and cross-linked polyvinylpyrrolidone are sieved through a 500 micron sieve and blended in a suitable mixer. The magnesium stearate is sieved through a 250 micron sieve and blended with the active blend. The blend is compressed into tablets using suitable punches.

| b) | Compound of the invention | 5.0 mg |
|---|---|---|
| | Lactose | 165.0 mg |
| | Pregelatinised Starch | 20.0 mg |
| | Cross-linked polyvinylpyrrolidone | 8.0 mg |
| | Magnesium Stearate | 2.0 mg |
| | Compression weight | 200.0 mg |

The compound of the invention, lactose and pregelatinised starch are blended together and granulated with water. The wet mass is dried and milled. The magnesium stearate and cross-linked polyvinylpyrrolidone are screened through a 250 micron sieve and blended with the granule. The resultant blend is compressed using suitable tablet punches.

| Example 42 - Capsules | | |
|---|---|---|
| a) | Compound of the invention | 5.0 mg |
| | Lactose | 193.0 mg |
| | Magnesium Stearate | 2.0 mg |
| | Fill weight | 200.0 mg |

The compound of the invention and pregelatinised starch are screened through a 500 micron mesh sieve, blended together and lubricated with magnesium stearate, (meshed through a 250 micron sieve). The blend is filled into hard gelatine capsules of a suitable size.

| b) | Compound of the invention | 5.0 mg |
|---|---|---|
| | Lactose | 177.0 mg |
| | Polyvinylpyrrolidone | 8.0 mg |
| | Cross-linked polyvinylpyrrolidone | 8.0 mg |
| | Magnesium Stearate | 2.0 mg |
| | Fill weight | 200.0 mg |

The compound of the invention and lactose are blended together and granulated with a solution of polyvinylpyrrolidone. The wet mass is dried and milled. The magnesium stearate and cross-linked polyvinylpyrrolidone are screened through a 250 micron sieve and blended with the granules. The resultant blend is filled into hard gelatine capsules of a suitable size.

| Example 43 - Syrup | | |
|---|---|---|
| a) | Compound of the invention | 5.0 mg |
| | Hydroxypropyl Methylcellulose | 45.0 mg |
| | Propyl Hydroxybenzoate | 1.5 mg |
| | Butyl Hydroxybenzoate | 0.75 mg |
| | Saccharin Sodium | 5.0 mg |
| | Sorbitol Solution | 1.0 ml |
| | Suitable Buffers | qs |
| | Suitable flavours | qs |
| | Purified Water to | 10.0 ml |

The hydroxypropyl methylcellulose is dispersed in a portion of hot purified water together with the hydroxybenzoates and the solution is allowed to cool to ambient temperature. The saccharin, sodium flavours and sorbitol solution are added to the bulk solution. The compound of the invention is dissolved in a portion of the remaining water and added to the bulk solution. Suitable buffers may be added to control the pH in the region of maximum stability. The solution is made up to volume, filtered and filled into suitable containers.

| Example 44 - Injection Formulation | |
|---|---|
| | % w/v |
| Compound of the invention | 1.00 |
| Water for injections B.P. to | 100.00 |

Sodium chloride may be added to adjust the tonicity of the solution and the pH may be adjusted to that of maximum stability and/or to facilitate solution of the compound of the invention using dilute acid or alkali or by the addition of suitable buffer salts. Solubilisers, such as cosolvents, may also be added to facilitate solution of the compound of the invention. Antioxidants and metal chelating salts may also be included. The solution is clarified, made up to final volume with water and the pH remeasured and adjusted if necessary, to provide 10 mg/ml of the compound of formula (I).

The solution may be packaged for injection, for example by filling and sealing in ampoules, vials or syringes. The ampoules, vials or syringes may be aseptically filled (e.g. the solution may be sterilised by filtration and filled into sterile ampoules under aseptic conditions) and/or terminally sterilised (e.g. by heating in an autoclave using one of the acceptable cycles). The solution may be packed under an inert atmosphere of nitrogen.

Preferably the solution is filled into ampoules, sealed by fusion of the glass and terminally sterilised.

Further sterile formulations are prepared in a similar manner containing 0.5, 2.0 and 5% w/v of the compound of the invention, so as to provide respectively 5, 20 and 50 mg/ml of the compound of the invention.

Biological Data

Inhibitory activity against human COX-1 and COX-2 was assessed in COS cells which had been stably transfected with cDNA for human COX-1 and human COX-2. 24 Hours prior to experiment, COS cells were transferred from the 175 $cm^2$ flasks in which they were grown, onto 24-well cell culture plates using the following procedure. The incubation medium (Dulbecco's modified eagles medium (DMEM) supplemented with heat-inactivated foetal calf serum (10% v/v), penicillin (100 IU/ml), streptomycin (100 $\mu$g/ml) and geneticin (600 $\mu$g/ml)) was removed from a flask of confluent cells (1 flask at confluency contains approximately $1 \times 10^7$ cells). 10 ml of phosphate buffered saline (PBS) was added to the flask to wash the cells. Having discarded the PBS, cells were then rinsed in 10 ml trypsin for 20 seconds, after which the trypsin was removed and the flask placed in an incubator (37°) for 1–2 minutes until cells became detached from the flask. The flask was then removed from the incubator and cells resuspended in 10 ml of fresh incubation medium. The contents of the flask was transferred to a 250 ml sterile container and the volume of incubation medium subsequently made up to 100 ml. 1 ml cell suspension was pipetted into each well of 4×24-well cell culture plates. The plates were then placed in an incubator (37° C., 95% air/5% $CO_2$) overnight. If more than 1 flask of cells were required, the cells from the individual flasks were combined before being dispensed into the 24-well plates.

Following the overnight incubation, the incubation medium was completely removed from the 24-well cell culture plates and replaced with 250 μl fresh DMEM (37° C.). The test compounds were made up to 250× the required test concentration in DMSO and were added to the wells in a volume of 1 μl. Plates were then mixed gently by swirling and then placed in an incubator for 1 hour (37° C., 95% air/5% $CO_2$). Following the incubation period, 10 μl of arachidonic acid (750 μM) was added to each well to give a final arachidonic acid concentration of 30 μM. Plates were then incubated for a further 15 minutes, after which the incubation medium was removed from each well of the plates and stored at −20° C., prior to determination of prostaglandin $E_2$ (PGE2) levels using enzyme immunoassay. The inhibitory potency of the test compound was expressed as an $IC_{50}$ value, which is defined as the concentration of the compound required to inhibit the PGE2 release from the cells by 50%. The selectivity ratio of inhibition of COX-1 versus COX-2 was calculated by comparing respective $IC_{50}$ values.

The following $IC_{50}$ values for inhibition of COX-2 and COX-1 were obtained for compounds of the invention:

| Example No. | COX-2: $IC_{50}$(nM) | COX-1: $IC_{50}$(nM) |
| --- | --- | --- |
| 1 | 1.3 | >100,000 |
| 2 | 10.8 | >100,000 |
| 3 | 2.5 | >100,000 |
| 4 | 0.25 | >100,000 |
| 9, 30 | 34 | >100,000 |
| 15, 31 | 0.28 | >100,000 |

What is claimed is:

1. A compound of formula (I)

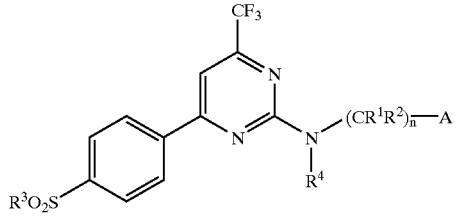

(I)

or a pharmaceutically acceptable salt or solvate thereof, in which:
$R^1$ and $R^2$ are independently selected from the group consisting of H and $C_{1-6}$alkyl;
$R^3$ is $C_{1-6}$alkyl or $NH_2$;
$R^4$ is H or $C_{1-6}$alkyl;
A is a 5- or 6-membered aryl, or a 5- or 6-membered aryl substituted by one or more $R^5$;
$R^5$ is halogen, $C_{1-6}$alkyl, $C_{1-6}$alkyl substituted by one or more F, $C_{1-6}$alkoxy, $C_{1-6}$alkoxy substituted by one or more F, $SO_2NH_2$ or $SO_2C_{1-6}$alkyl; and
n is 1 to 4.

2. A compound as claimed in claim 1 wherein $R^1$ and $R^2$ are independently selected from the group consisting of H and methyl.

3. A compound as claimed in claim 1 wherein $R^3$ is $C_{1-6}$alkyl.

4. A compound as claimed in claim 1 wherein $R^4$ is H or $C_{1-3}$alkyl.

5. A compound as claimed claim 1 wherein A is selected from the group consisting of:

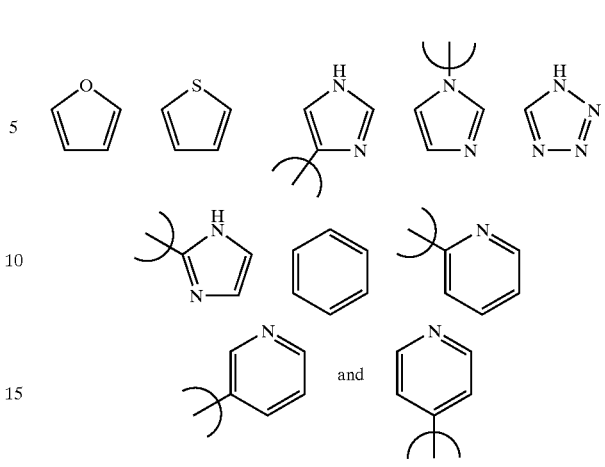

wherein A is unsubstituted or substituted by one or two $R^5$.

6. A compound as claimed in claim 1 wherein $R^5$ is halogen, $C_{1-3}$alkyl, $C_{1-3}$alkyl substituted by one to three F, $C_{1-3}$alkoxy, $C_{1-3}$alkoxy substituted by one to three F, or $SO_2NH_2$.

7. A compound as claimed in claim 1 wherein n is 1 to 3.

8. A compound as claimed in claim 1 wherein $R^1$ and $R^2$ are independently selected from the group consisting of H and methyl; $R^3$ is $C_{1-6}$alkyl; $R^4$ is H or $C_{1-3}$alkyl; A is selected from the group consisting of:

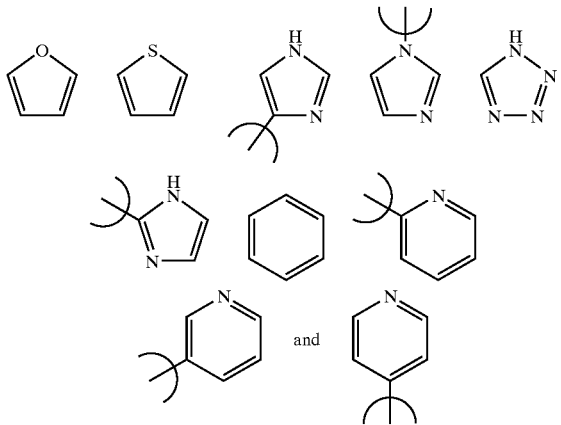

wherein A is unsubstituted or substituted by one or two $R^5$; $R^5$ is halogen, $C_{1-3}$alkyl, $C_{1-3}$alkyl substituted by one to three F, $C_{1-3}$alkoxy, $C_{1-3}$alkoxy substituted by one to three F, or $SO_2NH_2$; and n is 1 to 3.

9. A compound as claimed in claim 1 wherein A is selected from the group consisting of:

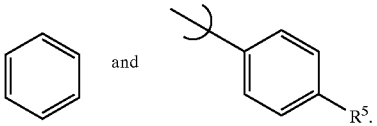

10. A compound as claimed in claim 1 wherein $R^6$ is halogen or $C_{1-6}$alkoxy.

11. A compound as claimed in claim 1 wherein $R^1$ and $R^2$ are both H.

12. A compound selected from the group consisting of:
4-[4-(methylsulfonyl)phenyl]-N-(pyridin-4-ylmethyl)-6-(trifluoromethyl)pyrimidin-2-amine;

4-[4-(methylsulfonyl)phenyl]-N-(pyridin-3-ylmethyl)-6-(trifluoromethyl)pyrimidin-2-amine;

4-[4-(methylsulfonyl)phenyl]-N-(pyridin-2-ylmethyl)-6-(trifluoromethyl)pyrimidin-2-amine;

4-[4-(methylsulfonyl)phenyl]-N-(phenylmethyl)-6-(trifluoromethyl)-2-pyrimidinamine;

N-(4-methoxybenzyl)-4-[4-(methylsulfonyl)phenyl]-6-(trifluoromethyl)pyrimidin-2-amine;

N-(4-fluorobenzyl)-4-[4-(methylsulfony)phenyl]-6-(trifluoromethyl)pyrimidin-2-amine;

and pharmaceutically acceptable salts or solvates thereof.

13. A compound as claimed in claim 1 wherein $R^3$ is $C_{1-3}$alkyl.

14. A compound as claimed in claim 1 wherein $R^3$ is methyl.

15. A compound as claimed in claim 1 wherein $R^4$ is H or methyl.

16. A compound as claimed claim 5 wherein A is unsubstituted or substituted by one $R^5$.

17. A compound as claimed in claim 1 wherein $R^5$ is selected from the group consisting of F, methyl, $CF_3$, methoxy, $OCHF_2$, $OCF_3$ and $SO_2NH_2$.

18. A compound as claimed in claim 1 wherein n is 1.

19. A compound as claimed in claim 1 wherein $R^1$ and $R^2$ are independently selected from the group consisting of H and methyl; $R^3$ is $C_{1-3}$alkyl; $R^4$ is H or methyl; A is selected from the group consisting of:

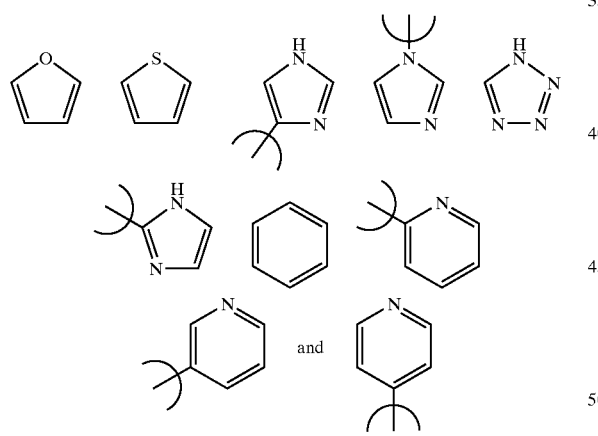

wherein A is unsubstituted or substituted by one $R^5$; $R^5$ is F, methyl, $CF_3$, methoxy, $OCHF_2$, $OCF_3$, and $SONH_2$; and n is 1.

20. A compound as claimed in claim 1 wherein $R^5$ is F or $C_{1-3}$alkoxy.

21. A compaund as claimed in claim 1 wherein $R^5$ is F or methoxy.

22. N-(4-fluorobenzyl)-4-[4-(methylsulfonyl)phenyl]-6-(trifluoromethyl)pyrimidin-2-amine or a pharmaceutically acceptable salt or solvate thereof.

23. A process for the preparation of a compound as defined in claim 1, which comprises the steps of:

a) reacting an amine of formula (II):

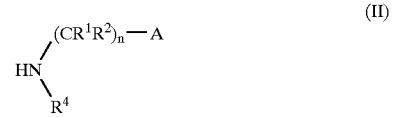

or a protected derivative thereof with a compound of formula (III):

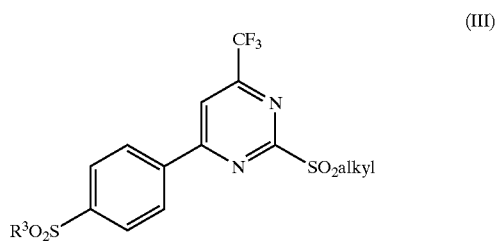

or a protected derivative thereof to prepare a compound of formula (I); and b) optionally converting the compound of formula (I) into a pharmaceutically acceptable salt or solvate thereof.

24. A process for the preparation of a compound as defined in claim 1, which comprises the steps of:

a) reacting an alkyl halide of formula (XII):

or a protected derivative thereof with a compound of formula (XI):

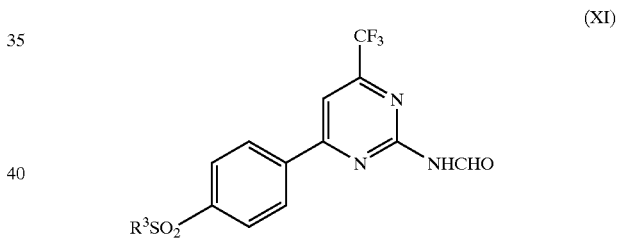

or a protected derivative thereof to prepare a compound of formula (I); and b) optionally converting the compound of formula (I) into a pharmaceutically acceptable salt or solvate thereof.

25. A process for the preparation of a compound as defined in claim 1, which comprises the steps of:

a) interconversion of a compound of formula (I) into another compound of formula (I) and b) optionally converting the compound of formula (I) into a pharmaceutically acceptable salt or solvate thereof.

26. A process for the preparation of a compound as defined in claim 1, which comprises the steps of:

a) deprotecting a protected derivative of a compound of formula (I); and b) optionally converting the compound of formula (I) into a pharmaceutically acceptable salt or solvate thereof.

27. A pharmaceutical composition comprising a compound as defined in claim 1 in admixture with one or more physiologically acceptable carriers or excipients.

28. A method of treating an animal subject suffering from a condition which is mediated by COX-2 which comprises administering to said subject an effective amount of a compound as defined in claim 1.

29. A method of treating an animal subject suffering from an inflammatory disorder, which method comprises administering to said subject an effective amount of a compound as defined in claim 1.

30. A method of treating a human subject suffering from a condition which is mediated by COX-2 which comprises administering to said subject an effective amount of a compound as defined in claim 1.

31. A method of treating a human subject suffering from an inflammatory disorder, which method comprises administering to said subject an effective amount of a compound as defined in claim 1.

32. The method according to claim 30, wherein said condition is selected from the group consisting of pain, fever and inflammation.

33. The method according to claim 30, wherein said condition is selected from the method according to rheumatic fever, symptoms associated with influenza or other viral infections, lower back and neck pain, headache, toothache, sprains, strains, myositis, sympathetically maintained pain, synovitis, arthritis, rheumatoid arthritis, degenerative joint diseases, osteoarthritis, gout, ankylosing spondylitis, tendinitis, bursitis, psoriasis, eczema, burns, dermatitis, sports injuries, injuries arising from surgical and dental procedures, neuropathic pain, diabetic neuropathy, sciatica, non-specific lower back pain, multiple sclerosis pain, fibromyalgia, HIV-related neuropathy, neuralgia, postherpetic neuralgia, trigeminal neuralgia, pain resulting from physical trauma, pain resulting from amputation, pain resulting from cancer, pain resulting from toxins, pain resulting from chronic inflammatory conditions, colonic cancer, prostate cancer, cancer associated with overexpression of HER-2/neu, breast cancer, stroke, epilepsy, epileptic seizures, dysmenorrhoea, premature labour, liver disease, inflammatory liver disease, asthma, allergic rhinitis, respiratory distress syndrome, inflammatory bowel disease, Crohn's disease, gastritis, irritable bowel syndrome, ulcerative colitis, inflammation in as vascular disease, inflammation in migraine, inflammation in periarteritis, inflammation in nodosa, inflammation in thyroiditis, inflammation in aplastic anaemia, inflammation in Hodgkin's disease, inflammation in sclerodoma, inflammation in type I diabetes, inflammation in myasthenia gravis, inflammation in multiple sclerosis, inflammation in sorcoidosis, inflammation in nephrotic syndrome, inflammation in Bechet's syndrome, inflammation in polymyositis, inflammation in gingivitis, inflammation in conjunctivitis and inflammation in myocardial ischemia, ophthalmic diseases, retinitis, retinopathies, uveitis, acute injury to the eye tissue, dementia, degenerative dementia, senile dementia, Alzheimer's disease, Pick's disease, Huntington's chorea, Parkinson's disease, Creutzfeldt-Jakob disease, vascular dementia, multi-infarct dementia, dementia associated with intracranial space occupying lesions, dementia associated with trauma, dementia associated with infections, dementia associated with HIV infection, dementia associated with metabolism, dementia associated with toxins, dementia associated with anoxia, dementia associated with vitamin deficiency, mild cognitive impairment associated with aging and Age Associated Memory Impairment.

34. The method according to claim 30, wherein said condition is arthritis.

35. The method according to claim 30, wherein said condition is selected from the group consisting of rheumatoid arthritis and osteoarthritis.

36. The method according to claim 30, wherein said condition is inflammation in migraine.

37. The method according to claim 30, wherein said condition is inflammation in multiple sclerosis or multiple sclerosis pain.

38. The method according to claim 30, wherein said condition is neuropathic pain.

39. A method of treating a human subject suffering from a condition which is mediated by COX-2 which comprises administering to said subject an effective amount of a compound as defined in claim 12.

40. The method according to claim 39, wherein said condition is arthritis.

41. The method according to claim 39, wherein said condition is selected from the group consisting of rheumatoid arthritis and osteoarthritis.

42. The method according to claim 39, wherein said condition is inflammation in migraine.

43. The method according to claim 39, wherein said condition is inflammation in multiple sclerosis or multiple sclerosis pain.

44. The method according to claim 39, wherein said condition is neuropathic pain.

45. A method of treating a human subject suffering from a condition which is mediated by COX-2 which comprises administering to said subject an effective amount of N-(4-fluorobenzyl)-4-[4-(methylsulfonyl)phenyl]-6-(trifluoromethyl)pyrimidin-2-amine or a pharmaceutically acceptable salt or solvate thereof.

46. The method according to claim 45, wherein said condition is arthritis.

47. The method according to claim 45, wherein said condition is selected from the group consisting of rheumatoid arthritis and osteoarthritis.

48. The method according to claim 45, wherein said condition is inflammation in migraine.

49. The method according to claim 45, wherein said condition is inflammation in multiple sclerosis or multiple sclerosis pain.

50. The method according to claim 45, wherein said condition is neuropathic pain.

* * * * *